(12) United States Patent
Li et al.

(10) Patent No.: US 12,156,882 B2
(45) Date of Patent: Dec. 3, 2024

(54) ANTI-AGING DRUG COMBINATION AND USE THEREOF

(71) Applicants: Xiamen Kingdomway Group Company, Fujian (CN); Inner Mongolia Kingdomway Pharceutical Limited, Inner Mongolia (CN); Kingdomway Biotech. (Jiangsu) Co., Ltd., Jiangsu (CN)

(72) Inventors: Dan Li, Fujian (CN); Fangfang Chen, Fujian (CN); Huaying Liu, Fujian (CN); Bingrong Wang, Fujian (CN); Weicheng Liao, Fujian (CN)

(73) Assignees: Xiamen Kingdomway Group Company, Fujian (CN); Inner Mongolia Kingdomway Pharceutical Limited, Inner Mongolia (CN); Kingdomway Biotech. (Jiangsu) Co., Ltd., Jiangsu (CN)

( * ) Notice: Subject to any disclaimer, the term of this patent is extended or adjusted under 35 U.S.C. 154(b) by 276 days.

(21) Appl. No.: 17/584,997

(22) Filed: Jan. 26, 2022

(65) Prior Publication Data

US 2023/0067269 A1 Mar. 2, 2023

(30) Foreign Application Priority Data

Aug. 30, 2021 (CN) .......................... 202111003974.1

(51) Int. Cl.
*A61K 31/706* (2006.01)
*A61K 9/50* (2006.01)
*A61K 33/04* (2006.01)
*A61K 33/08* (2006.01)
*A61K 33/30* (2006.01)
*A61K 36/06* (2006.01)
*A61K 45/06* (2006.01)

(52) U.S. Cl.
CPC .......... *A61K 31/706* (2013.01); *A61K 9/5015* (2013.01); *A61K 33/04* (2013.01); *A61K 33/08* (2013.01); *A61K 33/30* (2013.01); *A61K 36/06* (2013.01); *A61K 45/06* (2013.01)

(58) Field of Classification Search
CPC .......................... A61K 31/706; A61K 2300/00
See application file for complete search history.

(56) References Cited

U.S. PATENT DOCUMENTS

2021/0128593 A1* 5/2021 Palkar ........................ A61P 9/10
2021/0220422 A1* 7/2021 Parker .................... A61K 35/02

\* cited by examiner

*Primary Examiner* — Genevieve S Alley
(74) *Attorney, Agent, or Firm* — Howard & Howard Attorneys PLLC

(57) ABSTRACT

The present invention pertains to the field of nutrition and medicine, and relates to a drug combination for anti-aging and its use. Specifically, the present invention relates to a drug combination comprising: 0.5 to 30 parts by weight of NR or its pharmaceutically acceptable salt, 0.5 to 30 parts by weight of NMN, and 0.01 to 35 parts by weight of mineral. The drug combination of the present invention has good anti-oxidative or anti-aging effects, and has excellent stability.

18 Claims, No Drawings

ANTI-AGING DRUG COMBINATION AND USE THEREOF

CROSS-REFERENCE TO RELATED APPLICATIONS

The present application claims priority to and all the benefits of Chinese Application No. 202111003974.1 filed on Aug. 30, 20201, which is hereby expressly incorporated herein by reference in its entirety.

TECHNICAL FIELD

The invention pertains to the field of nutrition and medicine, and relates to an anti-aging drug combination composition and use thereof.

BACKGROUND ART

Aging is an activity that accompanies the occurrence and development of life. It occurs continuously from the fertilized egg to the death. Only at a certain stage does the characteristics of aging become more obvious. The physiological changes in the aging process of the human body are mainly reflected in the loss of tissue cells and constituent materials, the slowing down of the body's metabolic rate, and the decline of body and organ functions. Aging is inevitable, but it is possible to delay aging.

The mitochondria in human cells are the driving force for keeping human beings young. With the increase of age, the vitality of mitochondria becomes smaller and smaller. One of the most significant changes in the body's cells is the decrease of NAD+ level, which correlates the decrease NAD+ level to aging-related diseases. The full name of NAD+ is nicotinamide adenine dinucleotide, or coenzyme I for short. It is an important coenzyme of dehydrogenase in the human body, for example, alcohol dehydrogenase is used to oxidize ethanol and plays an irreplaceable role in glycolysis, gluconeogenesis, tricarboxylic acid cycle and respiratory chain, its intermediate product will pass the removed hydrogen to NAD, making it NADH, and NADH will act as a hydrogen carrier and be coupled through chemical permeation in the respiratory chain to synthesize ATP, which is a reducing agent and electron donor, participates in different cellular processes including oxidation and antioxidant systems, and participates in the mitochondrial oxidative metabolism process and acts as a signal molecule to ensure cell survival and regulate energy metabolism, cell repair and circadian rhythm, thereby existing in the form of coenzyme to regulate the physiological functions of various enzymes in cells. When the level of NAD+ decreases, it will cause the dysfunction of this series of processes in cells, leading to an increase in the level of intracellular inflammation, mitochondrial dysfunction, a series of enzyme dysfunctions that depend on NAD+, metabolic abnormality in cells, DNA damage and so on, thereby eventually leading to senescence of cells.

Because the molecular weight of NAD+ is too large, it is difficult to penetrate cell membrane to enter a cell, so that a cell can hardly take in it through oral administration, and thus it mainly depends on intracellular synthesis. NAD+ precursor substances include: tryptophan, niacin, nicotinamide, nicotinamide ribonucleoside, reduced nicotinamide ribonucleoside, nicotinamide mononucleotide, trigonelline, nicotinic acid mononucleotide, nicotinic acid ribonucleoside and so on. Studies have found that there are certain limitation levels of intake for niacin, nicotinamide and tryptophan, for example, the combination of niacin and GPR109A may cause severe flushing in patients, the excessive intake of tryptophan and nicotinamide may cause side effects, for example, nicotinamide may cause inhibition of deacetylase. Among the many supplemental NAD+ intermediates, nicotinamide ribose and nicotinamide mononucleotide are the most effective, which can be converted into NAD+ through the salvage synthesis pathway.

Nicotinamide ribose (hereinafter referred to as NR) is a precursor of an important coenzyme NAD+, and plays an important role in the energy production of human cells. It participates in intracellular synthesis of NAD+, can significantly improve cell viability, especially viability of senescent cells, has obvious improvement effects on the body's metabolism, immunity, brain function, cardiovascular function, etc., and can improve the body's overall function to make cells in vivo stay at a new active state, thereby achieving the purpose of delaying aging.

Nicotinamide mononucleotide is a naturally occurring biologically active nucleotide with two irregular forms, namely α and β, and β isomer is the active form of nicotinamide mononucleotide. β-nicotinamide mononucleotide (hereinafter referred to as NMN) is one of the key precursors of NAD+. Studies have shown that eating NMN can effectively increase in vivo content of NAD+ and significantly inhibit the metabolism caused by aging, making NMN an "everlasting elixir." In mammals, NMN is produced by nicotinamide under the catalysis of Nampt, and then NAD+ is produced from NMN under the catalysis of nicotinamide mononucleotide adenosyltransferase. Studies have found that by adjusting the in vivo level of NMN, it exhibits better treatment and repair effects on cardiovascular and cerebrovascular diseases, neurodegenerative diseases and aging degenerative diseases.

Minerals are one of the seven essential nutrients for the human body. The 7 essential minerals for the human body are calcium, phosphorus, magnesium, potassium, sodium, sulfur, and chlorine, which account for a content of more than 0.01% of the human body or a dietary intake of greater than 100 mg/d, and thus are called macro elements; while iron, zinc, copper, cobalt, molybdenum, selenium, iodine and chromium are 8 essential trace elements. Trace elements refer to minerals which accounts for a content of less than 0.01% of the human body or a dietary intake of less than 100 mg/d; in addition, manganese, silicon, nickel, boron and vanadium are t trace elements that may be necessary for the human body; furthermore, there are also some trace elements that are potentially toxic, their excessive intake may cause disease or damage to the human body, but they are also necessary trace elements for the human body at low doses, and these trace elements mainly include fluorine, lead, mercury, aluminum, arsenic, tin, lithium and cadmium. Minerals are the constituent elements of enzyme system in human body. The essential minerals of human body are the activity centers of many human enzymes. Among the thousands of enzymes discovered in the human body, more than 70% contain minerals or are related to minerals. Minerals can only be obtained by intake from the outside, and cannot be produced by human body itself. Minerals have the functions of improving anti-oxidation, killing free radicals and resisting aging in human body.

In the prior art, there is no research and report on the simultaneous use of NR, NMN and minerals.

CONTENTS OF THE INVENTION

After in-depth research and creative work, it is surprisingly found in the present invention that the combination of NR, NMN and minerals produces an unexpected synergistic effect in anti-oxidation and/or anti-aging, that is, the effect of taking the combination of the three is better than the sum of effects produced by using minerals alone and using (NR+NMN) alone. It is further found in the present invention that when NR or NMN is formulated into a conventional dosage form, it will become abnormally unstable in the presence of minerals, that is, it is found that minerals will accelerate the degradation of NR and NMN. Since NR and NMN are very expensive, this loss due to degradation is unacceptable. Thus, the following invention is provided:

One aspect of the present invention relates to a drug combination comprising:
  0.5 to 30 parts by weight of NR or its pharmaceutically acceptable salt,
  0.5 to 30 parts by weight of NMN, and
  0.01 to 35 parts by weight of mineral.

In some embodiments of the present invention, the drug combination comprises:
  0.7 to 30 parts by weight of NR or its pharmaceutically acceptable salt,
  0.8 to 30 parts by weight of NMN, and
  0.01 to 30 parts by weight of mineral.

In some embodiments of the present invention, the drug combination comprises:
  0.7 to 30 parts by weight of NR or its pharmaceutically acceptable salt,
  0.8 to 30 parts by weight of NMN, and
  1 to 30 parts by weight of mineral.

In some embodiments of the present invention, the drug combination comprises:
  0.5 to 25 parts by weight of NR or its pharmaceutically acceptable salt,
  0.5 to 25 parts by weight of NMN, and
  8 to 32 parts by weight of mineral.

In some embodiments of the present invention, the drug combination comprises:
  0.7 to 25 parts by weight of NR or its pharmaceutically acceptable salt,
  0.8 to 25 parts by weight of NMN, and
  8 to 32 parts by weight of mineral.

In some embodiments of the present invention, the drug combination comprises:
  0.7 to 24 parts by weight of NR or its pharmaceutically acceptable salt,
  0.8 to 21 parts by weight of NMN, and
  10 to 30 parts by weight of mineral.

In some embodiments of the present invention, the drug combination comprises:
  9 to 24 parts by weight of NR or its pharmaceutically acceptable salt,
  9 to 21 parts by weight of NMN, and
  10 to 20 parts by weight of mineral.

In some embodiments of the present invention, the drug combination comprises:
  9 parts by weight of NR or its pharmaceutically acceptable salt,
  9 parts by weight of NMN, and
  10 parts by weight of mineral.

In some embodiments of the present invention, in the drug combination, the pharmaceutically acceptable salt is NR chloride.

In some embodiments of the present invention, in the drug combination, NR or its pharmaceutically acceptable salt is 0.5 parts by weight, 0.7 parts by weight, 9 parts by weight, 24 parts by weight, or 25 parts by weight.

In some embodiments of the present invention, in the drug combination, NMN is 0.8 parts by weight, 9 parts by weight, 21 parts by weight, or 25 parts by weight.

In some embodiments of the present invention, in the drug combination, the mineral is 8 parts by weight, 10 parts by weight, 20 parts by weight, 30 parts by weight, or 32 parts by weight.

In some embodiments of the present invention, in the drug combination:
  the weight ratio of NR or its pharmaceutically acceptable salt to NMN is (1:30) to (30:1), preferably (1:10) to (10:1), (1:5) to (5:1), (1:4) to (4:1), (1:3) to (3:1), (1:2) to (2:1), (1:1.5) to (1.5:1); more preferably 1:1.

In some embodiments of the present invention, in the drug combination:
  the ratio of the sum of the weight of NR or its pharmaceutically acceptable salt and the weight of NMN to the weight of mineral is (0.5:1) to (1000:1), (0.5:1) to (250:1) or (0.5:1) to (30:1); preferably (0.5:1) to (3:1); more preferably (0.7:1) to (2.5:1), (1:1) to (2:1), 1.8:1, 0.7:1, 1.5:1 or 1.25:1.

In some embodiments of the present invention, in the drug combination:
  neither NR or its pharmaceutically acceptable salts nor NMN are in direct contact with mineral;
  preferably, NR or its pharmaceutically acceptable salt and NMN are simultaneously and/or separately contained in microcapsules;
  preferably, the microcapsules are enteric-coated microcapsules;
  preferably, the microcapsules further contain an antioxidant; preferably, the antioxidant is a water-soluble antioxidant and/or an oil-soluble antioxidant;
  preferably, the microcapsules are composed of a core material and at least two layers of wall materials, the core material comprises NR or its pharmaceutically acceptable salt and NMN, and the first layer wall material of the wall materials comprises a grease with a melting point higher than 38° C., which is coated on the outer surface of the core material, and the second layer wall material of the wall materials comprises a dispersible coating material, which is coated on the outer surface of the first layer wall material;
  preferably, the microcapsules are prepared by a method comprising the following steps:
  (1) dissolving NR or its pharmaceutically acceptable salt and NMN in water to obtain a water phase material;
  (2) mixing an emulsifier and a grease with a melting point higher than 38° C. evenly to obtain an oil phase material;
  (3) mixing the water phase material obtained in step (1) and the oil phase material obtained in step (2) and performing emulsification to obtain a water-in-oil emulsion;
  (4) dehydrating the water-in-oil emulsion obtained in step (3) to obtain a dehydrated water-in-oil emulsion; and
  (5) spraying the dehydrated water-in-oil emulsion obtained in step (4) into a fluidized bed for spray cooling and granulation to obtain microcapsules; preferably, continuously spraying and coating an enteric layer in the fluidized bed to obtain enteric-coated microcapsules.

In the above step (2), the emulsifier and the grease can be mixed in advance and then heated to melt, stirred and mixed evenly, or the grease can be melted first, and then mixed with the emulsifier evenly.

In the present invention, the grease with a melting point higher than 38° C. and the dispersible coating material are used as the embedding wall materials of the microcapsules for NR and NMN, so that compared with the traditional water-soluble colloids, the effect of isolating air is better, and the resistance to high temperature and humidity environment, grease environment and mechanical processing environment is greatly improved, thereby greatly improving the stability of the composition.

In one embodiment of the present invention, in the drug combination, the microcapsules are enteric-coated microcapsules, which can safely release NR and NMN in the intestinal tract through gastric juice to prevent them from being broken by gastric acid, thereby improving their absorption and utilization rates.

In some embodiments of the present invention, in the drug combination:
  the mineral comprises one or more selected from the group consisting of calcium, magnesium, zinc, selenium and chromium;
  preferably, the source of calcium is one or more selected from the group consisting of calcium oxide, calcium phosphate, calcium lactate, calcium citrate, calcium carbonate and calcium gluconate;
  preferably, the source of magnesium is one or more selected from the group consisting of magnesium sulfate, magnesium hydroxide and magnesium oxide;
  preferably, the source of zinc is one or more selected from the group consisting of zinc lactate, zinc chloride, zinc sulfate and zinc gluconate;
  preferably, the source of selenium is one or more selected from the group consisting of sodium selenite and selenium-enriched yeast;
  preferably, the source of chromium is one or more selected from the group consisting of chromium chloride, chromium pyridine, and chromium-enriched yeast;
  preferably, the mineral further comprises one or more selected from the group consisting of the group consisting of manganese (for example, manganese gluconate), sodium, potassium, iron and copper.

In some embodiments of the present invention, in the drug combination, based on the total weight of the mineral, the mineral comprises:
  800 to 1200 parts by weight of calcium, 120 to 1800 parts by weight of magnesium, 12 to 180 parts by weight of zinc, 0.05 to 1.5 parts by weight of selenium, 0.05 to 1.5 parts by weight of chromium, and optionally 0.5 to 5 parts by weight of manganese;
  preferably, comprises: 900 to 1100 parts by weight of calcium, 150 to 1500 parts by weight of magnesium, 15 to 150 parts by weight of zinc, 0.1-1 parts by weight of selenium, 0.1-1 parts by weight of chromium, and optionally 2 to 3 parts by weight of manganese;
  more preferably, comprises: 900 to 1100 parts by weight of calcium gluconate, 150 to 1500 parts by weight of magnesium oxide, 15 to 150 parts by weight of zinc gluconate, 0.1-1 parts by weight of selenium-enriched yeast, 0.1-1 parts by weight of chromium-enriched yeast, and optionally 2 to 3 parts by weight of manganese gluconate;
  particularly preferably, comprises:
  1000 parts by weight of calcium citrate, 150 parts by weight of magnesium sulfate, 15 parts by weight of zinc lactate, 0.1 parts by weight of sodium selenite, and 1 part by weight of chromium chloride; or
  1000 parts by weight of calcium carbonate, 1500 parts by weight of magnesium hydroxide, 150 parts by weight of zinc sulfate, 0.1 parts by weight of selenium-enriched yeast, and 0.1 parts by weight of chromium-enriched yeast; or
  1000 parts by weight of calcium gluconate, 150 parts by weight of magnesium oxide, 15 parts by weight of zinc gluconate, 0.1 parts by weight of selenium-enriched yeast, 0.1 parts by weight of chromium-enriched yeast, and 2.5 parts by weight of manganese gluconate.

In some embodiments of the present invention, the drug combination is a pharmaceutical composition;
  optionally, the pharmaceutical composition further comprises one or more pharmaceutically acceptable excipients;
  preferably, the pharmaceutical composition is a capsule, a tablet or a granule.

In some embodiments of the present invention, the drug combination is a combination product, comprising a first product and a second product that are individually packaged, wherein,
  the first product comprises NR or its pharmaceutically acceptable salt, and NMN;
  the second product comprises the mineral;
  preferably, the first product and the second product also independently comprise one or more pharmaceutically acceptable excipients;
  preferably, the first product and the second product are independently capsules, tablets or granules;
  preferably, the combination product also comprises a product instruction.

The drug combination according to any one of items of the present invention is used for anti-oxidation or anti-aging.

Another aspect of the present invention relates to a use of the drug combination described in any one of items of the present invention in the manufacture of a medicament for anti-oxidation or anti-aging.

Another aspect of the present invention relates to a method for anti-oxidation or anti-aging, comprising a step of administering an effective amount of the drug combination according to any one of items of the present invention to a subject in need.

In the present invention, for the weight or parts by weight of mineral, unless otherwise specified, calcium is calculated according to the weight or parts by weight of calcium salt, rather than the weight of calcium element. The weight or weight parts of other mineral such as calcium, zinc, selenium, chromium, manganese, etc. are all interpreted similarly.

In the present invention, for the sake of simplicity, the pharmaceutically acceptable salt comprises not only pharmaceutically acceptable salts but also nutritionally acceptable salts.

In the present invention, the mineral comprises inorganic mineral and/or organic mineral. The inorganic mineral is an inorganic salt, which is any pharmaceutically or nutritionally acceptable salt, such as carbonate, nitrate, halide, oxide, stearate, sulfate, phosphate, pyrophosphate, bicarbonate or dihydrophosphate; the organic mineral is a product of the combination of mineral and organic molecule, such as selenium-enriched yeast, chromium-enriched yeast, gluconate, citrate, lactate, etc.

In some embodiments of the present invention, the microcapsules, based on weight percentage (based on the total weight of the microcapsules), comprise: 1% to 30% NR or its pharmaceutically acceptable salt, 1% to 30% of NMN, 40% to 80% of a grease with melting point higher than 38° C., 5% to 15% of a surfactant, 5% to 25% of a dispersible coating material.

In the present invention, the pharmaceutically or nutritionally acceptable salt of NR is at least one selected from the group consisting of chloride, fluoride, oxide, bromide, hydration, formate, acetate, ascorbate, benzoate, carbonate, citrate, carbamate, formate, gluconate, lactate, methylbromide, methylsulfate, nitrate, phosphate, diphosphate, succinate, sulfate and difluoroacetate.

In the present invention, the grease with a melting point higher than 38° C. is at least one of wax, higher fatty acid, and hardened oil.

In the present invention, the wax can be animal wax, vegetable wax, mineral wax and synthetic wax, such as beeswax, insect wax, Sichuan wax, spermaceti wax, wool wax, palm wax, sumac wax, coconut wax, food-grade paraffin wax, ozokerite, microcrystalline wax, etc.

In the present invention, the higher fatty acid can be a C16 to C24 saturated or unsaturated fatty acid, such as stearic acid, palmitic acid, margaric acid, arachidic acid, behenic acid, etc.

In the present invention, the hardened oil can be hydrogenated cottonseed oil or hydrogenated soybean oil.

In the present invention, the surfactant is at least one selected from the group consisting of Tween, Span, sucrose fatty acid ester, lecithin, polyoxyethylene fatty acid ester, and polyglycerin fatty acid ester.

In the present invention, the dispersible coating material is at least one selected from the group consisting of silicon dioxide, calcium phosphate, calcium hydrogen phosphate, calcium carbonate, and starch; the starch may be corn starch, tapioca starch, potato starch, sweet potato starch, batata starch, etc.

Further, the microcapsules may also contain an antioxidant, the antioxidant accounts for 0.5% to 2% of the weight percentage of the microcapsules; the antioxidant may be a water-soluble antioxidant and/or oil-soluble antioxidant, the water-soluble antioxidant is mainly distributed in the core material of the microcapsules, the oil-soluble antioxidant is mainly distributed in the wall material of the microcapsules, and the two can exist at the same time, or only one of them can exist. Further, the antioxidant is at least one selected from the group consisting of coenzyme Q10, sodium erythorbate, ascorbyl palmitate, tea polyphenol, tocopherol, lipoic acid, BHT, BHA, TBHQ, and rosemary extract.

In the present invention, the microcapsules further comprise an enteric layer, and the enteric layer accounts for 2% to 20% of the weight of the microcapsules; the main component of the enteric layer is polyacrylic resin, including at least one of polyacrylic resin I, polyacrylic resin II, polyacrylic resin III, polyacrylic resin IV, L30D-55, L100D-55, E100/EPO, E12.5, L100, L12.5, S100, S12.5, FS30D.

Further, the enteric layer also comprises an anti-sticking agent and a plasticizer. Further, the main component of the anti-sticking agent is one or more of talc, diatomite, and silicon dioxide; the main component of the plasticizer is one or more of polyethylene glycol, triethyl citrate, glycerol triacetate, glycerin, and propylene glycol.

In some embodiments of the present invention, the preparation method of the microcapsules comprises:
(1) dissolving NR, NMN, and a water-soluble antioxidant (if any) in water to obtain a water phase material;
(2) mixing a surfactant and an oil-soluble antioxidant (if any) with a melted grease with a melting point higher than 38° C. to obtain an oil phase material;
(3) mixing the water phase material and the oil phase material and performing emulsification to obtain a water-in-oil emulsion;
(4) vacuum dehydrating the water-in-oil emulsion to obtain a dehydrated water-in-oil emulsion;
(5) spraying the dehydrated water-in-oil emulsion into a fluidized bed for spray cooling and granulation, and then sieving to obtain the microcapsules; wherein the fluidized bed is distributed with a fluidized dispersible coating material.

Further, in the above step (1), the amount of water is just enough to dissolve NR and NMN.

Further, in the above step (3), the emulsification method is at least one of high-speed shear method, high-pressure homogenization method, cavitation emulsification method, and microjet method.

Further, in the above step (4), the vacuum dehydration is performed at a vacuum degree of −0.05 MPa to −0.1 MPa.

Further, in the above steps (2) to (4), the temperature of the materials is controlled to be higher than 38° C.

Further, in the above step (5), the temperature of the material is controlled to be lower than 38° C., preferably lower than 30° C.

In one embodiment of the present invention, after the above step (5), the enteric layer is sprayed by a fluidized bed coating machine, and the temperature of the material is kept below 38° C. during this process.

In the present invention, the term "microcapsules" refers to small particles containing an active ingredient or core substance surrounded by a cover layer or shell.

In the present invention, unless otherwise specified, the "first" (for example, first product) and "second" (for example, second product) are used for the distinction or clarity of expression, and have no typical meaning of order.

BENEFICIAL EFFECTS OF THE PRESENT INVENTION

The present invention has achieved one or more of the following technical effects:
(1) good antioxidant effect, such as significantly reduced content of MDA and increased content of SOD in tissues;
(2) good anti-aging or anti-senility effects;
(3) The combined use of NR or its pharmaceutically acceptable salt and NMN (NR or its pharmaceutically acceptable salt+NMN) has a synergistic effect with minerals; the effect is better than using only NR or its pharmaceutically acceptable salt+NMN, or using only minerals.
(4) good stability;
(5) higher absorption rate.

SPECIFIC MODELS FOR CARRYING OUT THE INVENTION

The embodiments of the present invention will be described in detail below in conjunction with examples, but those skilled in the art will understand that the following examples are only used to illustrate the present invention and should not be regarded as limiting the scope of the present invention. If specific conditions were not indicated in the examples, it would be carried out in accordance with the conventional conditions or the conditions recommended by the manufacturer. The reagents or instruments used without the manufacturer's indication were all conventional products that were purchased commercially.

In the following examples, the content of NMN was detected by high performance liquid chromatography, wherein mobile phase A: 50 mmol/L potassium dihydrogen phosphate, mobile phase B: acetonitrile; chromatographic column: Agilent Zorbax SB-AQ, 250×4.6 mm; detection device: UV=254 nm; column temperature: 25° C.; flow rate: 1.0 mL/min; injection volume: 5 μL; gradient elution conditions: time/min (0, 4, 5, 6, 10), mobile phase A/vt % (96, 80, 80, 96, 96), mobile phase B/vt % (4, 20, 20, 4, 4). The content of NR was detected by high performance liquid chromatography, wherein C18 column (250 mm×4.6 mm, 5 m) was used as chromatographic column, methanol-buffer (pH 3.5, containing 0.1% sodium heptanesulfonate, 20:80, v/v) was used as mobile phase, flow rate was 1 mL/min, isocratic elution, column temperature was 30° C., and detection wavelength was 261 nm.

Example 1: Preparation of Microcapsules Containing NR and NMN (1) 1 Kg of NR chloride and 30 Kg of NMN were dissolved in 16 L of water to obtain a water phase material;
(2) 10 Kg of Tween-40, 5 Kg of Span-60 and 45 Kg of molten beeswax were mixed uniformly to obtain an oil phase material;
(3) the water phase material obtained in step (1) was added to the oil phase material obtained in step (2), and high-speed shear emulsification was performed for 30 minutes at 68° C. and shear speed of 9000 rpm to obtain a water-in-oil emulsion;
(4) the water-in-oil emulsion obtained in step (3) was dehydrated under a gradually increased vacuum at 68° C. and shear speed of 5000 rpm, until the vacuum degree reached −0.1 MPa and the water was substantially removed completely, and a dehydrated water-in-oil emulsion is obtained;
(5) the dehydrated water-in-oil emulsion obtained in step (4) was sprayed into a fluidized bed for spray cooling and granulation, wherein 9 Kg of fluidized silica was distributed in the fluidized bed, the temperature of material was controlled to keep at 25° C. during operation, and after sieving, 99.99 Kg of microcapsules containing NR and NMN were obtained. Through testing, the NR content was 1.03%, and the NMN content was 30.15%.

Example 2: Preparation of Microcapsules Containing NR and NMN (1) 30 Kg of NR chloride and 1 Kg of NMN were dissolved in 16 L of water to obtain a water phase material;
(2) 14 Kg of triglyceride monostearate and 50 Kg of molten palm wax were mixed uniformly to obtain an oil phase material;
(3) the water phase material obtained in step (1) was added into the oil phase material obtained in step (2), high-speed shear emulsification was performed at 86° C. and 10000 rpm shear speed for 15 min, and high pressure homogenization was performed at 45 MPa for 3 times to obtain a water-in-oil emulsion;
(4) the water-in-oil emulsion obtained in step (3) was dehydrated under gradually increased vacuum at 86° C. and 6000 rpm shear speed, until the vacuum reached −0.1 MPa and water was basically removed completely, to obtain a dehydrated water-in-oil emulsion;
(5) the dehydrated water-in-oil emulsion obtained in step (4) was sprayed into a fluidized bed for spray cooling and granulation, wherein 5 Kg of fluidized calcium phosphate was distributed in the fluidized bed, the temperature of the material was controlled to keep at 25° C. during operation, and after sieving, 99.95 Kg of microcapsules containing NR and NMN were obtained. Through testing, the NR content was 30.22%, and the NMN content was 1.13%.

Example 3: Preparation of Enteric-Coated Microcapsules Containing NR and NMN (1) 10 Kg of NR chloride and 10 Kg of NMN were dissolved in 10 L of water to obtain a water phase material;
(2) 2 Kg of lecithin, 8 Kg of Span-60 and 45 Kg of molten stearic acid were mixed uniformly to obtain an oil phase material;
(3) the water phase material obtained in step (1) and the oil phase material obtained in step (2) were simultaneously introduced into a multi-stage series cavitation emulsifier for emulsification, in the cavitation emulsifier, the temperature was 72° C. and the pressure was 300 MPa, and a water-in-oil emulsion was obtained;
(4) the water-in-oil emulsion obtained in step (3) was introduced into a wiped film evaporator, and continuous vacuum wiped film dehydration was performed at 75° C. and −0.08 MPa, until water was basically removed completely to obtain a dehydrated water-in-oil emulsion;
(5) the dehydrated water-in-oil emulsion obtained in step (4) was sprayed into a fluidized bed for spray cooling and granulation, wherein 10 Kg of fluidized corn starch was distributed in the fluidized bed, the temperature of material was controlled to keep at 25° C. to obtain microcapsules containing NR and NMN. 15 kg of enteric layer was continuously sprayed into the fluidized bed, wherein the formula of the enteric layer was 40% (w/w) polyacrylic resin III, 45% (w/w) L30D-55, 5% (w/w) glyceryl triacetate, 10% (w/w) talc, and the solvent used was an 80% (w/w) ethanol aqueous solution. During the operation, the temperature of material was controlled to keep at 30° C. After sieving, 99.90 Kg of enteric-coated microcapsules containing NR and NMN were obtained. Through testing, the content of NR was 10.06% and the content of NMN was 10.24%.

Example 4: Preparation of Microcapsules Containing NR and NMN (1) 15 Kg of NR, 15 Kg of NMN, and 0.6 Kg of sodium erythorbate were dissolved in 16 L of water to obtain a water phase material;
(2) 5 Kg of PEG-40 hydrogenated castor oil, 0.4 Kg of tocopherol and 59 Kg of molten palmitic acid were mixed uniformly to obtain an oil phase material;
(3) the water phase material obtained in step (1) and the oil phase material obtained in step (2) were introduced into a microjet emulsifier for continuous emulsification at an emulsification temperature of 65° C. to obtain a water-in-oil emulsion;
(4) the water-in-oil emulsion obtained in step (3) was introduced into a wiped film evaporator, and continuous vacuum wiped film dehydration was performed at 65° C. and −0.1 MPa, until water was basically removed completely, to obtain a dehydrated water-in-oil emulsion;

(5) the dehydrated water-in-oil emulsion obtained in step (4) was sprayed into a fluidized bed for spray cooling and granulation, wherein 5 Kg of fluidized cassava starch was distributed in the fluidized bed, the temperature of material was controlled to keep at 25° C. during operation, and after sieving, 99.70 Kg of microcapsules containing NR and NMN were obtained. Through testing, the NR content was 14.93%, and the NMN content was 15.01%.

Example 5: Preparation of Microcapsules Containing NR and NMN (1) 20 Kg of NR, 5 Kg of NMN, and 0.3 Kg of tea polyphenol were dissolved in 13 L of water to obtain a water phase material;
(2) 10 Kg of sucrose ester SE-15, 0.2 Kg of ascorbyl palmitate and 40 Kg of molten hydrogenated cottonseed oil were mixed uniformly to obtain an oil phase material;
(3) the water phase material obtained in step (1) was added to the oil phase material obtained in step (2), and high-speed shear emulsification was performed at 75° C. and shear speed of 12000 rpm for 20 minutes to obtain a water-in-oil emulsion;
(4) the water-in-oil emulsion obtained in step (3) was dehydrated under gradually increased vacuum at 75° C. and shear speed of 6000 rpm, until the vacuum degree reached −0.1 MPa and water was basically removed completely, to obtain a dehydrated water-in-oil emulsion;
(5) the water-in-oil emulsion obtained in step (4) was sprayed into a fluidized bed for spray cooling and granulation, wherein 24.5 Kg of fluidized calcium hydrogen phosphate was distributed in the fluidized bed, the temperature of material was controlled to keep at 25° C., and after sieving, 99.96 Kg of microcapsules containing NR and NMN were obtained. Through testing, the NR content was 19.67%, and the NMN content was 5.16%.

Example 6: Preparation of Microcapsules Containing NR and NMN (1) 50 Kg of NR and 50 Kg of NMN were dissolved in 50 L water to obtain a water phase material;
(2) 50 Kg of Span-20, 20 Kg of coenzyme Q10 and 780 Kg of molten hydrogenated soybean oil were mixed uniformly to obtain an oil phase material;
(3) the water phase material obtained in step (1) was added to the oil phase material obtained in step (2), and high-speed shear emulsification was performed at 75° C. and shear speed of 9000 rpm for 30 minutes to obtain a water-in-oil emulsion;
(4) the water-in-oil emulsion obtained in step (3) was dehydrated under gradually increased vacuum at 75° C. and shear speed of 5000 rpm, until the vacuum degree reached −0.09 MPa and water was basically removed completely to obtain a dehydrated water-in-oil emulsion;
(5) the dehydrated water-in-oil emulsion obtained in step (4) was sprayed into a fluidized bed for spray cooling and granulation, wherein 50 Kg of fluidized silica and corn starch were distributed in the fluidized bed (their mass ratio was 1:1), the temperature of material was controlled to keep at 25° C. during operation, and after sieving, 998.36 Kg of microcapsules containing NR and NMN were obtained. Through testing, the NR content was 4.93%, and the NMN content was 5.06%.

Example 7 to Example 18: Preparation of Drug Combinations

Minerals, microcapsules containing NR and NMN were accurately weighed according to Table 1 below, and mixed thoroughly to obtain drug combinations.

TABLE 1

| | Mineral | | Microcapsules containing NR and NMN | | |
|---|---|---|---|---|---|
| | Proportion of mineral (weight parts) | Weight | Example/ dosage | NR weight | NMN weight |
| Example 7 | 1000 parts of calcium carbonate<br>150 parts of magnesium oxide<br>15 parts of zinc lactate<br>0.1 parts of sodium selenite<br>0.1 parts of chromium chloride | 0.01 Kg | Example 6/ 99.99 Kg | about 5 Kg | about 5 Kg |
| Example 8 | 1000 parts of calcium oxide<br>1500 parts of magnesium oxide<br>15 parts of zinc lactate<br>0.1 parts of sodium selenite<br>0.1 parts of chromium chloride | 0.1 Kg | Example 5/ 99.9 Kg | about 20 Kg | about 5 Kg |
| Example 9 | 1000 parts of calcium phosphate<br>150 parts of magnesium sulfate<br>150 parts of zinc gluconate<br>0.1 parts of sodium selenite<br>0.1 parts of chromium chloride | 1 Kg | Example 4/ 99 Kg | about 15 Kg | about 15 Kg |
| Example 10 | 1000 parts of calcium lactate<br>150 parts of magnesium sulfate<br>15 parts of zinc gluconate<br>1 part of sodium selenite<br>0.1 parts of chromium pyridine | 10 Kg | Example 3/ 90 Kg | about 9 Kg | about 9 Kg |
| Example 11 | 1000 parts of calcium citrate<br>150 parts of magnesium sulfate<br>15 parts of zinc lactate<br>0.1 parts of sodium selenite<br>1 part of chromium chloride | 20 Kg | Example 2/ 80 Kg | about 24 Kg | about 0.8 Kg |

TABLE 1-continued

| | Mineral | | Microcapsules containing NR and NMN | | |
|---|---|---|---|---|---|
| | Proportion of mineral (weight parts) | Weight | Example/ dosage | NR weight | NMN weight |
| Example 12 | 1000 parts of calcium carbonate<br>1500 parts of magnesium hydroxide<br>150 parts of zinc sulfate<br>0.1 parts of selenium-enriched yeast<br>0.1 parts of chromium-enriched yeast | 30 Kg | Example 1/ 70 Kg | about 0.7 Kg | about 21 Kg |
| Example 13 | 1000 parts of calcium gluconate<br>1500 parts of magnesium oxide<br>150 parts of zinc chloride<br>1 part of selenium-enriched yeast<br>0.1 parts of chromium-enriched yeast | 15 Kg | Example 3/ 85 Kg | about 8.5 Kg | about 8.5 Kg |
| Example 14 | 1000 parts of calcium gluconate<br>1500 parts of magnesium oxide<br>150 parts of zinc chloride<br>1 part of selenium-enriched yeast<br>1 part of chromium-enriched yeast | 5 Kg | Example 3/ 95 Kg | about 9.5 Kg | about 9.5 Kg |
| Example 15 | 1000 parts of calcium gluconate<br>150 parts of magnesium oxide<br>15 parts of zinc gluconate<br>0.1 parts of selenium-enriched yeast<br>0.1 parts of chromium-enriched yeast<br>2.5 parts of manganese gluconate | 10 Kg | Example 3/ 90 Kg | about 9 Kg | about 9 Kg |
| Example 16 | 1000 parts of calcium citrate<br>150 parts of magnesium oxide<br>15 parts of zinc gluconate<br>0.1 parts of selenium-enriched yeast<br>0.1 parts of chromium-enriched yeast<br>1 part copper citrate | 4.5 Kg | Example 3/ 95.5 Kg | about 9.55 Kg | about 9.55 Kg |
| Example 17 | 1000 parts of calcium gluconate<br>150 parts of magnesium oxide<br>15 parts of zinc gluconate<br>0.1 parts of selenium-enriched yeast<br>0.1 parts of chromium-enriched yeast<br>7.5 parts of ferrous lactate | 10 Kg | Example 3/ 90 Kg | about 9 Kg | about 9 Kg |
| Example 18 | 1000 parts of calcium gluconate<br>150 parts of magnesium oxide<br>15 parts of zinc gluconate<br>0.1 parts of selenium-enriched yeast<br>0.1 parts of chromium-enriched yeast<br>2.5 parts of manganese gluconate<br>1 part copper citrate<br>7.5 parts of ferrous lactate<br>1000 parts of potassium chloride<br>1000 parts of sodium chloride | 10 Kg | Example 3/ 90 Kg | about 9 Kg | about 9 Kg |

Example 19: Preparation of Vegetarian Soft Capsules (1) 15 parts of hyproxypropylmethylcellulose, 10 parts of polyethylene glycol, 0.5 parts of citric acid, 5 parts of ethanol and 25 parts of water were mixed to obtain a premixed solution;
(2) the premixed solution was mixed with 5 parts of chitosan at 90° C. to obtain a glue solution;
(3) the glue solution was degassed under vacuum condition;
(4) 150 parts of the drug combination of Example 7 was taken as the content of soft capsules;
(5) an automatic rotary capsule-making machine was used to press the content and the degassed glue solution into pellets, and then they were blown and shaped in a net machine at 20° C.; after being shaped for 4 hours, they were trimmed and washed with ethanol in a pellet-washing machine to remove a surface oil layer on the soft capsules, then they were blown again in a net machine for 6 hours to obtain dried soft capsules;
(6) the dried soft capsules were sorted to remove large pellets, small pellets, abnormally shaped pellets, pellets with obvious net imprinting, leaked pellets, flat pellets, thin-walled pellets, bubble pellets, etc. so as to obtain vegetarian soft capsules.

Example 20: Preparation of Tablets

Tablet formulation: as shown in Table 2 below.

TABLE 2

| Component | Weight parts |
|---|---|
| The drug combination of Example 8 | 30 |
| Mannitol | 39 |
| Microcrystalline cellulose | 15 |
| Hydroxypropylmethylcellulose | 10 |

TABLE 2-continued

| Component | Weight parts |
| --- | --- |
| Crospovidone | 1.5 |
| Sucralose | 2 |
| Sodium stearyl fumarate | 2.5 |
| Total | 100 |

Preparation method: the components other than sodium stearyl fumarate were weighed according to their prescription portions, sieved and transferred to a mixing barrel, mixed at 15 rpm for 30 minutes, then added with sodium stearyl fumarate and mixed for 5 minutes, and tabletting was performed to obtain tablets with a hardness of 35N to 50N.

Experimental Example 1: Stability Test

1. Experimental Samples
   Sample 1: The drug combination prepared in Example 15;
   Sample 1-1: The microcapsules in Example 15 were replaced with raw materials of NR and NMN that were not embedded, that was, the composition of Sample 1-1 was: 10 Kg of mineral (which formula was the same as that of Example 15), 9 Kg of NR chlorine, 9 Kg of NMN, the above-mentioned substances were accurately weighed and mixed well to obtain Sample 1-1.
   Sample 1-2: the microcapsules in Example 15 were replaced with microcapsules prepared by the following traditional technical method:
   10 Kg of NR chloride, 10 Kg of NMN, 45 Kg of sodium starch octenyl succinate were dissolved in 55 L of water to obtain a water phase material; 2 Kg of lecithin and 8 Kg of Span-60 were mixed uniformly to obtain an oil phase material; the water phase material and the oil phase material as above obtained were simultaneously introduced into a multi-stage series cavitation emulsifier for emulsification, the cavitation emulsifier had a temperature of 72° C. and a pressure of 300 MPa to obtain an emulsion; the above emulsion was sprayed into a fluidized bed for adsorption and granulation, 10 Kg of fluidized corn starch was distributed in the fluidized bed, so as to obtain microcapsules embedded with corn starch on the surface, and fluidized drying was performed at 60° C. to obtain microcapsules containing NR and NMN. In the fluidized bed, 15 kg of enteric layer was continuously sprayed for coating, the formula of the enteric layer was: 40% (w/w) polyacrylic resin III, 45% (w/w) L30D-55, 5% (w/w) glyceryl triacetate, 10% (w/w) talc, and the solvent used was an 80% (w/w) ethanol aqueous solution, the temperature of material is controlled to keep at 30° C. during the operation, and after sieving, Sample 1-2 was obtained.

That was, the composition of Sample 1-2 was: 10 Kg of mineral (which formula was the same as that of Example 15), and 90 Kg of microcapsules were prepared by the above method. The above-mentioned substances were accurately weighed and mixed evenly to obtain the composition.

Sample 1-3: 9 Kg of NR chloride, 9 Kg of NMN, the above-mentioned substances were accurately weighed, and mixed well to obtain Sample 1-3.

2. Experimental Method

According to the guidelines of formulation stability experiments in the Chinese Pharmacopoeia, 2015 version, the samples were placed in sealed brown vials and subjected to stability tests of long-term (25° C., 60% RH) and accelerated conditions (40° C., 75% RH).

Retention rate=content at the end of storage/initial content*100%.

3. Experimental Results
   As shown in Table 3.

TABLE 3

| | Retention rates of NR and NMN (% w/w) Temperature/Humidity | | | | | | | | |
| --- | --- | --- | --- | --- | --- | --- | --- | --- | --- |
| | | | 25° C./60% RH | | | | 40° C./75% RH | | |
| | | | | | Time | | | | |
| | Initial | | 1 month | | 3 months | | 1 month | | 3 months | |
| | NR | NMN | NR | NMN | NR | NMN | NR | NMN | NR | NMN |
| Sample 1 | 100 | 100 | 99.0 | 99.3 | 98.3 | 98.5 | 98.6 | 98.4 | 96.2 | 97.5 |
| Sample 1-1 | 100 | 100 | 51.6 | 66.7 | 34.6 | 57.5 | 38.7 | 50.4 | 17.3 | 33.2 |
| Sample 1-2 | 100 | 100 | 88.4 | 91.3 | 86.1 | 87.7 | 78.6 | 81.5 | 62.6 | 70.4 |
| Sample 1-3 | 100 | 100 | 56.9 | 71.1 | 45.5 | 66.0 | 48.6 | 58.7 | 32.2 | 48.1 |

It could be seen from the experimental results of Samples 1-1 and 1-3 that minerals had a negative effect on the stability of NR and NMN, and minerals would accelerate the degradation of NR and NMN.

From the experimental results of Sample 1, Sample 1-2 and Sample 1-1, it could be seen that the stability of NR and NMN were greatly improved by first microencapsulating NR and NMN and then mixing with minerals.

From the experimental results of Sample 1 and Sample 1-2, it could be seen that the microcapsules prepared by the present invention were more stable than those prepared by traditional methods in the prior art, and the stability of composition was significantly improved in comparison with traditional water-soluble colloids. The present inventors speculated that the microcapsules prepared by the present invention could better isolate air and/or better withstand high temperature and high humidity environments.

Experimental Example 2: Anti-Aging Effect Test

Malondialdehyde (MDA) is a lipid peroxidation product, and is closely related to the production of free radicals in the body and the degree of lipid peroxidation of tissues and cells in the body, so that it can reflect the oxidative stress damage state of tissues in the body, and is one of the important indicators for evaluating aging. Superoxide dismutase (SOD) is a key enzyme for scavenging oxygen free radicals in the body, and its activity can reflect the antioxidant capacity of tissues, so that it is also an important indicator for evaluating body aging.

(1) Model Building, Administration and Experimental Grouping

Modeling: 140 Wistar rats, weighing 120.36 g±2.35 g, half male and half male, were randomly divided into 14 groups, each with 10 rats. Except for the blank control group, rats in the other groups were injected with 5% D-galactose, 120 mg/kg, subcutaneously into neck every day so as to build aging model.

Administration: Intragastric administration was performed for 30 days from the 13$^{th}$ day of modeling, and the administration volume of each group was 2 mL. After each administration, the rats were subjected to fasting without water deprivation for 24 hours, blood was taken from eye ground, the blood was allowed to stand at room temperature until the blood was completely coagulated, then centrifuged to separate serum for later use. Then the rats were killed by dislocation method, liver and brain tissues were quickly separated, washed with sodium chloride solution and processed to obtain 10% tissue homogenate, which was centrifuged to obtain a tissue homogenate supernatant for later use. Xanthine oxidase method and thiobarbituric acid spectrophotometry were respectively used to determine SOD activity and MDA content in serum, liver and brain tissues.

Experiment Grouping:
a. Blank control group: normal saline;
b. Model control group: normal saline;
c. Example 15 drug group: The composition of Example 15 and physiological saline were taken to prepare a suspension with a concentration of 2.0 g/mL (i.e., the concentration of NR was 0.18 g/mL, the concentration of NMN was 0.18 g/mL, and the concentration of mineral was 0.2 g/mL);
d. Comparative group 1: The microcapsules were the same as in Example 15, but no mineral was added, that was, only there were only microcapsules but no mineral, and physiological saline was added to form a suspension with a concentration of 1.8 g/mL (i.e., the concentrations of NR and NMN were the same as those of Group c);
e. Comparative group 2: The mineral was the same as in Example 15, but no microcapsules were added, that was, there was only mineral but no microcapsules, and physiological saline was added to form a solution with a concentration of 0.2 g/mL (i.e., the concentration of mineral was the same as tat of Group c).
f. Example 11 drug group: The composition of Example 11 and physiological saline were taken to prepare a suspension with a concentration of 2.0 g/mL (i.e., the concentration of NR was 0.48 g/mL, the concentration of NMN was 0.016 g/mL, and the concentration of mineral was 0.4 g/mL);
g. Comparative group 3: The microcapsules were the same as in Example 11, but no mineral was added, that was, there were only microcapsules but no mineral, and physiological saline was added to form a suspension with a concentration of 1.6 g/mL (i.e., the concentrations of NR and NMN were the same as those of Group f);
h. Comparative group 4: The mineral was the same as in Example 11, but no microcapsules were added, that was, there was only mineral but no microcapsules, and physiological saline was added to form a solution with a concentration of 0.4 g/mL (i.e., the concentration of mineral was the same as that of Group f).
i. Example 12 drug Group: The composition of Example 12 and physiological saline were taken to prepare a suspension with a concentration of 2.0 g/mL (i.e., the concentration of NR was 0.014 g/mL, the concentration of NMN was 0.42 g/mL, and the concentration of mineral was 0.6 g/mL);
j. Comparative group 5: The microcapsules were the same as in Example 12, but no mineral was added, that was, there were only microcapsules but no mineral, and physiological saline was added to form a suspension with a concentration of 1.4 g/mL (i.e., the concentrations of NR and NMN were the same as those of Group i);
k. Comparative group 6: The mineral was the same as in Example 12, but no microcapsules were added, that was, there was only mineral but no microcapsules, and physiological saline was added to form a solution with a concentration of 0.6 g/mL (i.e., the concentration of mineral was the same as that of Group i).
l. Example 7 drug Group: The composition of Example 7 was added with physiological saline to prepare a suspension with a concentration of 2.0 g/mL (i.e., the concentration of NR was 0.10 g/mL, the concentration of NMN was 0.10 g/mL, and the concentration of mineral was 0.0002 g/mL);
m. Example 8 drug group: The composition of Example 8 was added with physiological saline to prepare a suspension with a concentration of 2.0 g/mL (i.e., the concentration of NR was 0.40 g/mL, the concentration of NMN was 0.10 g/mL, and the concentration of mineral was 0.002 g/mL);
n. Example 9 drug Group: The composition of Example 9 was added with physiological saline to prepare a suspension with a concentration of 2.0 g/mL (i.e., the concentration of NR was 0.30 g/mL, the concentration of NMN was 0.30 g/mL, and the concentration of mineral was 0.02 g/mL);

(2) Experimental Results

As shown in Table 4 and Table 5.

TABLE 4

| | MDA content (nmol/ml) | | | | | |
|---|---|---|---|---|---|---|
| Group | Serum | Reduction (%, vs Model control group) | Liver | Reduction (%, vs Model control group) | Brain | Reduction (%, vs Model control group) |
| Blank control group | 6.74 ± 0.96 | 55.3 | 3.09 ± 0.74 | 63.4 | 3.48 ± 0.69 | 68.6 |
| Model control group | 15.07 ± 3.06 | — | 8.45 ± 0.99 | — | 11.08 ± 2.22 | — |
| Example 15 drug group | 6.54 ± 0.77 | 56.6 | 3.26 ± 0.66 | 61.4 | 3.68 ± 0.78 | 66.8 |

TABLE 4-continued

| Group | MDA content (nmol/ml) | | | | | |
|---|---|---|---|---|---|---|
| | Serum | Reduction (%, vs Model control group) | Liver | Reduction (%, vs Model control group) | Brain | Reduction (%, vs Model control group) |
| Comparative group 1 | 8.97 ± 0.85 | 40.5 | 4.80 ± 0.73 | 43.2 | 7.37 ± 0.96 | 33.5 |
| Comparative group 2 | 14.26 ± 2.35 | 5.4 | 7.70 ± 1.02 | 8.9 | 9.96 ± 1.25 | 10.1 |
| Example 11 drug group | 7.49 ± 0.74 | 50.3 | 3.73 ± 0.63 | 55.8 | 4.32 ± 0.67 | 61.0 |
| Comparative group 3 | 9.67 ± 0.86 | 35.8 | 5.14 ± 0.71 | 39.2 | 7.59 ± 0.98 | 31.5 |
| Comparative group 4 | 14.37 ± 1.98 | 4.6 | 7.82 ± 0.87 | 7.5 | 10.05 ± 1.04 | 9.3 |
| Example 12 drug group | 6.96 ± 0.66 | 53.8 | 3.58 ± 0.51 | 57.6 | 4.03 ± 0.66 | 63.6 |
| Comparative group 5 | 9.25 ± 1.13 | 38.6 | 5.03 ± 0.45 | 40.5 | 7.43 ± 0.75 | 32.9 |
| Comparative group 6 | 14.41 ± 2.04 | 4.4 | 7.77 ± 0.91 | 8.0 | 10.10 ± 1.12 | 8.8 |
| Example 7 drug group | 8.57 ± 0.78 | 43.1 | 4.55 ± 0.82 | 46.2 | 6.40 ± 0.67 | 42.2 |
| Example 8 drug group | 8.15 ± 0.81 | 45.9 | 4.28 ± 0.75 | 49.3 | 5.64 ± 0.71 | 49.1 |
| Example 9 drug group | 7.72 ± 0.76 | 48.8 | 3.97 ± 0.70 | 53.0 | 5.02 ± 0.76 | 54.7 |

TABLE 5

| Group | SOD content (U/ml) | | | | | |
|---|---|---|---|---|---|---|
| | Serum | Increase (%, vs Model control group) | Liver | Increase (%, vs Model control group) | Brain | Increase (%, vs Model control group) |
| Blank control group | 170.62 ± 16.24 | 98.0 | 139.26 ± 12.57 | 67.9 | 71.67 ± 9.50 | 51.2 |
| Model control group | 86.17 ± 10.40 | — | 82.94 ± 11.34 | — | 47.40 ± 3.68 | — |
| Example 15 drug group | 169.33 ± 18.36 | 96.5 | 137.10 ± 11.65 | 65.3 | 70.15 ± 7.78 | 48.0 |
| Comparative group 1 | 148.73 ± 18.93 | 72.6 | 119.52 ± 13.42 | 44.1 | 63.33 ± 5.27 | 33.6 |
| Comparative group 2 | 93.75 ± 12.66 | 8.8 | 87.58 ± 9.64 | 5.6 | 50.34 ± 5.62 | 6.2 |
| Example 11 drug group | 165.79 ± 16.54 | 92.4 | 133.87 ± 11.42 | 61.4 | 68.11 ± 6.14 | 43.7 |
| Comparative group 3 | 147.61 ± 15.36 | 71.3 | 117.44 ± 12.13 | 41.6 | 61.86 ± 5.62 | 30.5 |
| Comparative group 4 | 92.63 ± 11.45 | 7.5 | 88.08 ± 9.34 | 6.2 | 49.96 ± 5.03 | 5.4 |
| Example 12 drug group | 167.34 ± 18.35 | 94.2 | 134.78 ± 12.61 | 62.5 | 69.01 ± 6.36 | 45.6 |
| Comparative group 5 | 146.40 ± 16.24 | 69.9 | 118.11 ± 10.63 | 42.4 | 62.96 ± 5.33 | 32.8 |
| Comparative group 6 | 94.27 ± 10.65 | 9.4 | 87.83 ± 9.46 | 5.9 | 50.15 ± 5.64 | 5.8 |
| Example 7 drug group | 150.04 ± 16.33 | 74.1 | 122.15 ± 12.67 | 47.3 | 64.51 ± 5.26 | 36.1 |
| Example 8 drug group | 153.47 ± 17.62 | 78.1 | 124.56 ± 11.53 | 50.2 | 65.17 ± 5.48 | 37.5 |
| Example 9 drug group | 157.93 ± 16.46 | 83.3 | 128.89 ± 12.42 | 55.4 | 66.12 ± 5.69 | 39.5 |

The results showed that there was no statistical difference in MDA content and serum SOD activity between the drug groups of the present invention and the blank control group, indicating that the drug combination of the present invention could effectively enhance the body's ability to resist oxidation and scavenging free radicals, and reduce the damage degree of tissue cells, and these indicators could be basically restored to the levels before the aging model was built.

The study also found that the comparative groups all had MDA contents higher than those of the drug groups of the present invention (P<0.05), and all had SOD activity lower than those of the drug groups of the present invention (P<0.05), indicating that their antioxidative and anti-aging effects were not as good as those of the drug groups of the present invention, and indicating that the combination of the present invention was the best, that was, the absence of any one of the ingredients would reduce the antioxidative and anti-aging effects.

It could be seen from Table 4 that Comparative group 1 using microcapsules containing NR and NMN alone showed reduced MDA in serum, liver and brain by a percentage of 40.5%, 43.2% and 33.5%, respectively; Comparative group 2 using mineral alone showed reduced MDA in serum, liver and brain by a percentage of 5.4%, 8.9% and 10.1%, respectively; while the data of Example 15 drug group of the present invention showed that when the microcapsules containing NR and NMN were used in combination with mineral, the MDA in serum, liver and brain is reduced by a percentage of 56.6%, 61.4%, and 66.8%, respectively, which were all significantly higher than the corresponding sums of simple addition of the MDA reduction effects of Control group 1 and Control group 2, i.e., 45.9% (40.5%+5.4%), 52.1% (43.2%+8.9%) and 43.6% (33.5%+10.1%). Similar experimental results were also observed when comparing Example 11 drug group of the present invention with Comparative group 3 and Comparative group 4, and comparing Example 12 drug group of the present invention with Comparative group 5 and Comparative group 6. It could be seen that the drug combination of the present invention had a significant effect in reducing MDA, and the combination of (NR+NMN) and mineral had a synergistic effect compared with single use of (NR+NMN) or single use of mineral.

It could be seen from Table 5 that Comparative group 1 using the microcapsules containing NR and NMN alone showed increased SOD in serum, liver, and brain by a percentage of 72.6%, 44.1% and 33.6%, respectively; Comparative group 2 using mineral alone showed increased SOD in serum, liver, and brain by a percentage of 8.8%, 5.6%, and 6.2%, respectively. The data of the drug groups of the present invention showed that when the microcapsules containing NR and NMN were used in combination with mineral, the SOD in serum, liver, and brain were increased by 96.5%, 65.3%, and 48.0%, respectively, which were all significantly higher than the corresponding sums of simple addition of the SOD increasing effects of Comparative group 1 and Comparative group 2, i.e., 81.4% (72.6%+8.8%), 49.7% (44.1%+5.6%), and 39.8% (33.6%+6.2%). Similar experimental results were also observed when comparing Example 11 drug group of the present invention with Comparative group 3 and Comparative group 4, and comparing Example 12 drug group of the present invention with Comparative group 5 and Comparative group 6. It could be seen that the drug combination of the present invention had a significant effect in increasing SOD, and the combination of (NR+NMN) and mineral had a synergistic effect compared with single use of (NR+NMN) or single use of mineral.

Although the specific embodiments of the present invention have been described in detail, those skilled in the art will understand that according to all the teachings that have been disclosed, various modifications and substitutions can be made to those details, and these changes are all within the protection scope of the present invention. The full scope of the invention is given by the appended claims and any equivalents thereof.

What is claimed is:

1. A drug combination, comprising:
   0.5 to 30 parts by weight of nicotinamide ribose (NR) or its pharmaceutically acceptable salt,
   0.5 to 30 parts by weight of 0-nicotinamide mononucleotide (NMN), and
   0.01 to 35 parts by weight of mineral, wherein the mineral comprises 900 to 1100 parts by weight of calcium gluconate, 150 to 1500 parts by weight of magnesium oxide, 15 to 150 parts by weight of zinc gluconate, 0.1 to 1 parts by weight of selenium-enriched yeast, and 0.1 to 1 parts by weight of chromium-enriched yeast.

2. The drug combination according to claim 1, comprising:
   0.7 to 30 parts by weight of NR or its pharmaceutically acceptable salt,
   0.8 to 30 parts by weight of NMN, and
   0.01 to 30 parts by weight of mineral.

3. The drug combination according to claim 1, wherein the pharmaceutically acceptable salt is NR chloride.

4. The drug combination according to claim 1, wherein: the weight ratio of NR or its pharmaceutically acceptable salt to NMN is (1:30) to (30:1).

5. The drug combination according to claim 1, wherein: the ratio of the sum of the weight of NR or its pharmaceutically acceptable salt and the weight of NMN to the weight of mineral is (0.5:1) to (1000:1).

6. The drug combination according to claim 1, wherein: neither NR or its pharmaceutically acceptable salt nor NMN are in direct contact with mineral.

7. The drug combination according to claim 1, which is a pharmaceutical composition comprising one or more pharmaceutically acceptable excipients; and
   is a capsule, a tablet or a granule.

8. The drug combination according to claim 1, which is a combination product, comprising a first product and a second product that are individually packaged,
   wherein,
   the first product comprises NR or its pharmaceutically acceptable salt and NMN; and
   the second product comprises mineral.

9. The drug combination according to claim 1, comprising:
   0.7 to 30 parts by weight of NR or its pharmaceutically acceptable salt,
   0.8 to 30 parts by weight of NMN, and
   1 to 30 parts by weight of mineral.

10. The drug combination according to claim 1, comprising:
    0.5 to 25 parts by weight of NR or its pharmaceutically acceptable salt,
    0.5 to 25 parts by weight of NMN, and
    8 to 32 parts by weight of mineral.

11. The drug combination according to claim 1, wherein: the weight ratio of NR or its pharmaceutically acceptable salt to NMN is (1:3) to (3:1).

12. The drug combination according to claim 1, wherein: the ratio of the sum of the weight of NR or its pharmaceutically acceptable salt and the weight of NMN to the weight of mineral is (0.5:1) to (3:1).

13. The drug combination according to claim 1, wherein: NR or its pharmaceutically acceptable salt and NMN are simultaneously and/or separately contained in microcapsules containing an antioxidant selected from a water-soluble antioxidant and an oil-soluble antioxidant.

14. The drug combination according to claim 13, wherein: the microcapsules are composed of a core material and at least two layers of wall materials, the core material comprises NR or its pharmaceutically acceptable salt and NMN, the first layer wall material of the wall materials comprises a grease with a melting point higher than 38° C. which is coated on the outer surface of the core material, and the second layer wall material of the wall materials comprises a dispersible coating material which is coated on the outer surface of the first layer wall material.

15. The drug combination according to claim 14, wherein: according to weight percentage based on the microcapsules, the microcapsules comprise: 1% to 30% of NR or its pharmaceutically acceptable salt, 1% to 30% of NMN, 40% to 80% of a grease with a melting point higher than 38° C., 5% to 15% of a surfactant, and 5% to 25% of a dispersible coating material.

16. The drug combination according to claim 1, wherein: the microcapsules are prepared by a method comprising the following steps:
    (1) dissolving NR or its pharmaceutically acceptable salts and NMN in water to prepare a water phase material;
    (2) mixing uniformly an emulsifier and a grease with a melting point higher than 38° C. to obtain an oil phase material;
    (3) mixing the water phase material obtained in step (1) and the oil phase material obtained in step (2) and performing emulsification to obtain a water-in-oil emulsion;
    (4) dehydrating the water-in-oil emulsion obtained in step (3) to obtain a dehydrated water-in-oil emulsion; and
    (5) spraying the dehydrated water-in-oil emulsion obtained in step (4) into a fluidized bed for spray cooling and granulation to obtain microcapsules.

17. The drug combination according to claim 16, wherein:
spraying the dehydrated water-in-oil emulsion in step (5) comprises continuously spraying an enteric layer onto the microcapsules in the fluidized bed to obtain enteric-coated microcapsules.

18. A method for anti-oxidation or anti-aging, comprising a step of administering an effective amount of the drug combination according to claim 1 to a subject.

\* \* \* \* \*